(12) United States Patent
Fischer et al.

(10) Patent No.: US 12,202,802 B2
(45) Date of Patent: Jan. 21, 2025

(54) STYRYL QUINOLINIUM, PROCESS FOR THEIR PREPARATION AND USE THEREOF AS FLUORESCENT PROBES FOR IMAGING

(71) Applicant: BAR ILAN UNIVERSITY, Ramat Gan (IL)

(72) Inventors: Bilha Fischer, Shoham (IL); Abed Elhady Saady, Bu'eine Nujeidat (IL); Yaron Shav-Tal, Elkana (IL); Eli Varon, Nehalim (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 297 days.

(21) Appl. No.: 17/507,028

(22) Filed: Oct. 21, 2021

(65) Prior Publication Data

US 2022/0119349 A1 Apr. 21, 2022

Related U.S. Application Data

(60) Provisional application No. 63/094,360, filed on Oct. 21, 2020.

(51) Int. Cl.
| | |
|---|---|
| *C07D 215/10* | (2006.01) |
| *C07D 215/14* | (2006.01) |
| *G01N 1/30* | (2006.01) |
| *G01N 21/64* | (2006.01) |

(52) U.S. Cl.
CPC ......... *C07D 215/10* (2013.01); *C07D 215/14* (2013.01); *G01N 1/30* (2013.01); *G01N 21/6458* (2013.01); *G01N 21/6486* (2013.01); *G01N 2001/302* (2013.01)

(58) Field of Classification Search
CPC .................................................. C07D 215/10
See application file for complete search history.

(56) References Cited

U.S. PATENT DOCUMENTS 7,338,428 B2 * 3/2008 Chang ................... C09B 23/145
506/15

OTHER PUBLICATIONS

Görner, Journal of Photochemistry and Photobiology, A: Chemistry (2011), 218(2-3), 199-203. (Year: 2011).*
Tanaka et al., Crystal Growth & Design (Aug. 2019), 19(10), 5811-5818. (Year: 2019).*
Seiad, L. L.; Villemin, D.; Bar, N.; Hachemi, M., Solvent-Free condensation of methyl pyridinium and quinolinium salts with aldehydes catalyzed by DBU. Synth. Commun. 2012, 42 (5), 650-657.
Ramani, A.; Chanda, B.; Velu, S.; Sivasanker, S., One-pot synthesis of coumarins. Catalysis by the solid base, calcined Mg—Al hydrotalcite. Green Chem 1999, 1 (3), 163-165.
Li, Y.; Xu, D.; Ho, S.-L.; Li, H.-W.; Yang, R.; Wong, M. S., A theranostic agent for in vivo near-infrared imaging of β-amyloid species and inhibition of β-amyloid aggregation. Biomaterials 2016, 94, 84-92.
Teshome, A.; Bhuiyan, M. D. H.; Gainsford, G. J.; Ashraf, M.; Asselberghs, I.; Williams, G. V.; Kay, A. J.; Clays, K., Synthesis, linear and quadratic nonlinear optical properties of ionic indoline and N, N-dimethylaniline based chromophores. Opt. Mater 2011, 33 (3), 336-345.
Ashwell, G. J.; Mohib, A., Improved molecular rectification from selfassembled monolayers of a sterically hindered dye. J. Am. Chem. Soc 2005, 127 (46), 16238-16244.
Dondoni, A.; Massi, A.; Minghini, E.; Bertolasi, V., Dihydropyridine C-Glycoconjugates by Hantzsch Cyclocondensation. Synthesis of a C (6)-Glycosylated Nifedipine Analogue. Helv. Chim. Acta 2002, 85 (10), 3331-3348.
Saunders, J., Top Drugs: Top Synthetic Routes. Oxford Chemistry Primers 2002, 90 (1).
Taylor Jr, R.; Markley, E.; Ellenbogen, L., The inhibition of monoamine oxidase by styrylquinoliniums. Biochem. Pharmacol. 1967, 16 (1), 79-86.
Kumar, R.; Långström, B.; Darreh-Shori, T., Novel ligands of Choline Acetyltransferase designed by in silico molecular docking, hologram QSAR and lead optimization. Sci Rep 2016, 6, 31247.
Fortuna, C. G.; Barresi, V.; Musso, N.; Musumarra, G., Synthesis and applications of new trans 1-indolyl-2-(1-methyl byridinium and quinolinium-2-yl) ethylenes. Arkivoc 2009, 8, 222-229.
Jones G. The knoevengel Condensation. Org React 2004; 15; 204-599.
Saady et al., Applying styryl quinolinium fluorescent probes for imaging of ribosomal RNA in living cells, Dyes and Pigments, 174:(107986)1-12 (2020) , Available online Oct. 23, 2019.

* cited by examiner

*Primary Examiner* — Laura L Stockton
(74) *Attorney, Agent, or Firm* — FISHERBROYLES, LLP; Roger L. Browdy (57) ABSTRACT

The present invention is directed to styryl quinolinium compounds, a process for their synthesis and their use for selective nucleoli staining in cells, preferably in living cells and for imaging rRNA.

2 Claims, 7 Drawing Sheets

STYRYL QUINOLINIUM, PROCESS FOR THEIR PREPARATION AND USE THEREOF AS FLUORESCENT PROBES FOR IMAGING

TECHNOLOGICAL FIELD

The present invention concerns styryl quinolinium compounds, their preparation and use as fluorescent probes for imaging, by rapid and selective stain of nucleoli in both fixed and living cells.

BACKGROUND ART

References considered to be relevant as background to the presently disclosed subject matter are listed below:

Seiad, L. L.; Villemin, D.; Bar, N.; Hachemi, M., Solvent-Free condensation of methyl pyridinium and quinolinium salts with aldehydes catalyzed by DBU. *Synth. Commun.* 2012, 42 (5), 650-657.

Ramani, A.; Chanda, B.; Velu, S.; Sivasanker, S., One-pot synthesis of coumarins. Catalysis by the solid base, calcined Mg—Al hydrotalcite. *Green Chem* 1999, 1 (3), 163-165.

Li, Y.; Xu, D.; Ho, S.-L.; Li, H.-W.; Yang, R.; Wong, M. S., A theranostic agent for in vivo near-infrared imaging of β-amyloid species and inhibition of β-amyloid aggregation. *Biomaterials* 2016, 94, 84-92.

Teshome, A.; Bhuiyan, M. D. H.; Gainsford, G. J.; Ashraf, M.; Asselberghs, I.; Williams, G. V.; Kay, A. J.; Clays, K., Synthesis, linear and quadratic nonlinear optical properties of ionic indoline and N, N-dimethylaniline based chromophores. *Opt. Mater* 2011, 33 (3), 336-345.

Ashwell, G. J.; Mohib, A., Improved molecular rectification from self-assembled monolayers of a sterically hindered dye. *J. Am. Chem. Soc* 2005, 127 (46), 16238-16244.

Dondoni, A.; Massi, A.; Minghini, E.; Bertolasi, V., Dihydropyridine C-Glycoconjugates by Hantzsch Cyclocondensation. Synthesis of a C (6)-Glycosylated Nifedipine Analogue. *Helv. Chim. Acta* 2002, 85 (10), 3331-3348.

Saunders, J., Top Drugs: Top Synthetic Routes. *Oxford Chemistry Primers* 2002, 90 (1).

Taylor Jr, R.; Markley, E.; Ellenbogen, L., The inhibition of monoamine oxidase by styrylquinoliniums. *Biochem. Pharmacol.* 1967, 16 (1), 79-86.

Kumar, R.; Långström, B.; Darreh-Shori, T., Novel ligands of Choline Acetyltransferase designed by in silico molecular docking, hologram QSAR and lead optimization. *Sci Rep* 2016, 6, 31247.

Fortuna, C. G.; Barresi, V.; Musso, N.; Musumarra, G., Synthesis and applications of new trans 1-indolyl-2-(1-methyl pyridinium and quinolinium-2-yl) ethylenes. *Arkivoc* 2009, 8, 222-229.

Jones G. The knoevengel Condensation. Org React 2004; 15; 204-599.

Acknowledgement of the above references herein is not to be inferred as meaning that these are in any way relevant to the patentability of the presently disclosed subject matter.

BACKGROUND

Dyes emitting at long wavelengths, green to red regions have are used in various applications, including visualization of biomolecules in living systems, real-time tracking of cellular events, and fluorescent dye guidance during surgeries. These applications are based on the minimal autofluorescence of cells at wavelengths above 600 nm, the penetration depths of NIR-dyes, as well as their sensitivity and minimal photo-damage on cells and tissues. Styryl quinolinium- and merocyanine-dye classes constitute scaffolds that are applied for the development of NIR dyes for the above applications of visualization of biomolecules, tracking cellular events and guidance during surgery. Other uses of styryl-quinolinium derivatives are used in therapeutic treatment of various conditions. Specific 1-methyl-4-(substituted) styryl-quinolinium analogs are used for treatment of tuberculosis, other styryl quinolinium derivatives are used as choline acetyltransferase inhibitors or in antitumor activity.

Specifically, a styryl quinolinium dye contains two non-identical aryl groups usually joined by an ethylene moiety. One of the aryl groups is electron deficient (e.g., pyridinium moiety) while the other one is electron rich, thus resulting in a push-pull system. Unlike the positively charged styryl quinolinium dyes, merocyanine dyes are zwitterions and hence are essentially neutral. Merocyanine push-pull dyes contain two ethylene-bridged aryl groups, one of which is positively charged (e.g., pyridinium moiety) and the other one is negatively charged (e.g., phenolate moiety). In particular, merocyanine dyes are used for detection of DNA or RNA since they often exhibit enhanced fluorescence intensity by binding to nucleic acids.

Various dyes have been reported for selective nucleoli staining, however, there remain a demand for new fluorescent dyes that are photochemically stable easily synthesized and purified and stain the nucleoli rapidly.

GENERAL DESCRIPTION

The present invention is based on the findings of a new family of styryl quinolinium compounds, an improved process for their facile and high yield synthesis and their use for selective nucleoli staining in cells, preferably in living cells and for imaging rRNA.

In a first aspect, the present invention is directed to a compound of formula (I):

wherein:
$R_1$, $R_2$, $R_3$, $R_4$, $R_5$ are independently selected from H, F, Cl, Br, I, OR, NHR, $NR_2$, CN, $R'SO_3$, $(R')_4N$, $(R')_3NH$, $NO_2$.

R is independently selected from H or straight or branched $C_{1-6}$alkyl;

R' is straight or branched $C_{1-6}$ alkyl; and

X is Cl, Br, I;

provided that:
in case $R_3$ is Cl, then one of $R_1$, $R_2$, $R_4$, $R_5$ is not H;
in case $R_3$ is $N(CH_3)_2$, then one of $R_1$, $R_2$, $R_4$, $R_5$ is not H;
in case $R_2$ and $R_3$ are both $OCH_3$, then one of $R_1$, $R_4$, $R_5$ is not H.

More particularly, $R_1$ is H, F, Cl, or OR, $R_2$ is H, F, Cl, OR, $NO_2$ or CN, $R_3$ is H, OR, NHR or $NR_2$, $R_4$ is H, F, Cl, CN, $NO_2$, $R_5$ is H, F, Cl; R being H, or straight or branched $C_{1-6}$alkyl and X is I.

In a further aspect the present invention is directed to a process for the synthesis of a compound of formula (I) by reacting compound of formula (II) with a compound of formula (III) in the presence of a base in an appropriate solvent under heating:

In particular, the base is a pyridine or piperidine, the alcohol is ethanol and heating is done by microwave irradiation at a temperature of 70-80° C.

Yet in a further aspect the present invention is directed to the use of the styryl quinolinium compounds of the present invention for staining cells, particularly living cells and fluorescent probes for imaging, particularly rRNA.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 4A-D: provides spectrum scan showing peak of excitation/emission.

FIGS. 5A-C: Compound I-e rapidly stains living HeLa cells and does not affect viability.

FIGS. 6A-B: Compound I-e binds to RNA in cells.

FIGS. 7A-B: demonstrates the binding of compound I-e to rRNA in cells.

DETAILED DESCRIPTION OF EMBODIMENTS

The present invention is directed to styryl quinolinium compounds of formula (I), their synthesis and use. The unique process of synthesis by employing microwave irradiation provides a much higher yield than refluxing the solvent and a shorter duration of the reaction.

Straight or branched alkyl groups according to the present application are straight or branched —$CH_3$, —$C_2H_5$, $C_3H_7$, $C_4H_9$, $C_5H_{11}$, $C_6H_{13}$ groups.

Generally, the synthesis of the styryl quinolinium compounds of formula (I), was conducted by the following path (Knoevenagel condensation):

Where heating varied from 5-40 minutes in a microwave at a temperature of 65° C.-85° C. or for 5-20 hours under reflux. The former process is superior by its yield and duration. The base may be selected from pyridine, piperidine, the $C_{1-4}$alcohol is selected from methanol, ethanol, propanol, isopropanol, butanol, sec-butyl alcohol, tert-butyl alcohol.

More particularly, the reaction was carried in the presence of piperidine in ethanol in a microwave as follows:

In particular, specific compounds of formula (I) are:
(E)-2-(4-hydroxystyryl)-1-methylquinolinium iodide (I-a);
(E)-2-(4-Methoxystyryl)-1-methylquinolinium iodide (I-b);
(E)-2-(3-Fluoro-4-hydroxystyryl)-1-methylquinolinium iodide (I-c);
(E)-2-(3-Fluoro-4-methoxystyryl)-1-methylquinolinium iodide (I-d);
(E)-2-(3, 5-Difluoro-4-hydroxystyryl)-1-methylquinolinium iodide (I-e);
(E)-2-(3, 5-Difluoro-4-methoxystyryl)-1-methylquinolinium iodide (I-f);
(E)-2-(2,3,5,6-Tetrafluoro-4-hydroxystyryl)-1-methylquinolinium iodide (I-g);
(E)-2-(2,3,5,6-Tetrafluoro-4-methoxystyryl)-1-methylquinolinium iodide (I-h);
(E)-2-(4-Dimethylaminostyryl)-1-methylquinolinium iodide (I-i);
(E)-2-(3,4-Dihydroxystyryl)-1-methylquinolinium iodide (I-j);
(E)-2-(2-Hydroxy-3-methoxy-5-nitrostyryl)-1-methylquinolinium iodide (I-k); and
(E)-2-(4-Hydroxy-3-nitrostyryl)-1-methylquinolinium iodide (I-l).

The compounds, depending on their substituents vary in their properties such as their solubility, absorbance wavelength, quantum yield and photostability. These properties vary depending on the nature of the solvent as well. The styryl quinolinium compounds of formula (I), were found to be nontoxic to leaving cells and therefore may be used for staining cells, particularly living cells and fluorescent probes for imaging, particularly RNA. The compounds of the present invention display unique and specific properties when stain and dye living cells. The compounds clearly show preference to binding to secondary structures in the rRNA, wherein under heating when the secondary structure disappears, binding is lost.

The invention will now be described with reference to the following non-limiting Examples and drawings.

Example 1: Chemical Synthesis

A mixture of compounds (II) and (III) was irradiated at a temperature of about 65° C.-85° C. To a 10 mL microwave reaction vessel equipped with a magnetic stirring bar were added 1,4-dimethyl quinolinium iodide ((II); 0.5 mmol), absolute ethanol (5 mL), piperidine (cat. amount), and a substituted benzaldehyde ((III); 0.5 mmol). Thus 3,5-Difluoro-4-hydroxybenzaldehyde, or 2,3,5,6-Tetrafluoro-4-hydroxybenzaldehyde (whose $^1$H NMR, $^{13}$C NMR, $^{19}$F NMR and High Resolution Mass Spectrum (HRMS) are given below are exemplified. The vessel was sealed, and the mixture was irradiated in a microwave oven (CEM Focused Microwave type Discover) for 5 to 30 min at 70-80° C. (as indicated in Table 1). Then the reaction mixture was cooled to RT, and diethyl ether (10 mL) was added to precipitate the products as black crystals. The latter were vacuum-filtered and washed 3×3 mL with diethyl ether to yield pure products. In a similar manner all compounds I-a-I-l were isolated in a high yield, >95% purity e as determined by 1H NMR, $^{13}$C NMR, 19F NMR, DEPT, UV and HRMS.

Following are the $^1$H NMR, $^{13}$C NMR and/or 19F NMR and HRMS of compounds of two compounds of formula (III) and of the I-a-I-l styryl quinolinium compounds.

3,5-Difluoro-4-hydroxybenzaldehyde. $^1$H-NMR (400 MHZ, CDCl$_3$): 9.82 (t, J=1.8 Hz, 1H), 7.49 (d, J=6.4 Hz, 2H). $^{13}$C NMR (ppm): 190.93, 152.32, 137.15, 132.74, 111.53. $^{19}$F NMR (376 MHz, CDCl$_3$) δ −135.14 ppm. HRMS Calcd for $C_7H_4F_2O_2$ m/z 158.03035, Found 158.03024.

2,3,5,6-Tetrafluoro-4-hydroxybenzaldehyde. $^1$H NMR (DMSO, 400 MHZ): δ 10.22 (s, 1H), 3.36 (bs, 1H). $^{13}$C NMR (DMSO 75.45 MHz): δ 91.5, 98.7, 136.1, 139.5, 143.2, 146.5, 182.3. Calcd for $C_7H_2F_4O_2$ m/z 194.09183, Found 193.09189.

I-a (E)-2-(4-hydroxystyryl)-1-methylquinolinium iodide (I-a). $^1$H-NMR (400 MHz, DMSO (d6)): 8.97 (d, 5.89 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 2H, Ar), 4.31 (s, 3H, $^+$NCH$_3$). $^{13}$C NMR (ppm): 157.71, 157.32, 142.85, 132.54, 130.83, 130.52, 129.98, 129.54, 128.14, 126.91, 126.71, 125.02, 123.82, 119.87, 116.16, 115.95, 46.92. HRMS Calcd for $C_{18}H_{16}NOI$ m/z 389.23025, Found 389.23024.

I-b (E)-2-(4-Methoxystyryl)-1-methylquinolinium iodide (I-b). $^1$H-NMR (400 MHz, DMSO (d6)): 8.96 (d, 5.89 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 2H, Ar), 4.31 (s, 3H, $^+$NCH$_3$), 3.92 (s, 3H, OCH$_3$). $^{13}$C NMR (ppm): 157.71, 157.32, 142.85, 132.54, 130.83, 130.52, 129.98, 129.54, 128.14, 126.91, 126.71, 125.02, 123.82, 119.87, 116.16, 115.95, 55.52, 46.92. HRMS Calcd for $C_{19}H_{18}NOI$ m/z 403.48018, Found 403.48026.

I-c (E)-2-(3-Fluoro-4-hydroxystyryl)-1-methylquinolinium iodide (I-c). $^1$H-NMR (400 MHZ, DMSO (d6)): 9.06 (d, 5.89 Hz, 1H, Ar), 8.68 (d, 8.5 Hz, 1H, Ar), 8.43 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 2H, Ar), 4.31 (s, 3H, $^+$NCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 45.32. $^{19}$F NMR −130.94 ppm. HRMS Calcd for $C_{18}H_{15}FNOI$ m/z 407.22431, Found 407.21909.

I-d (E)-2-(3-Fluoro-4-methoxystyryl)-1-methylquinolinium iodide (I-d). 1H-NMR (400 MHZ, DMSO (d6)): 9.06 (d, 5.89 Hz, 1H, Ar), 8.68 (d, 8.5 Hz, 1H, Ar), 8.43 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 1H, Ar), 4.31 (s, 3H, $^+$NCH$_3$), 3.82 (s, 3H, OCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 55.23, 45.32. $^{19}$F NMR −129.83 ppm. HRMS Calcd for $C_{19}H_{17}FNOI$ m/z 421.49363, Found 421.51019.

I-e

(E)-2-(3,5-Difluoro-4-hydroxystyryl)-1-methylquinolinium iodide (I-e). 1H-NMR (400 MHZ, DMSO (d6)): 9.02 (d, 5.8 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 4.31 (s, 3H, $^+$NCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 45.32. $^{19}$F NMR−133.13 ppm. HRMS Calcd for $C_{18}H_{14}F_2NOI$ m/z 425.22031, Found 425.21901.

I-f

(E)-2-(3,5-Difluoro-4-methoxystyryl)-1-methylquinolinium iodide (I-f). $^1$H-NMR (400 MHZ, DMSO (d6)): 9.02 (d, 5.8 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 4.31 (s, 3H, $^+$NCH$_3$), 3.83 (s, 3H, OCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 62.35, 45.32. $^{19}$F NMR −133.13 ppm. HRMS Calcd for $C_{19}H_{16}F_2NOI$ m/z 439.14021, Found 439.15001.

I-g (E)-2-(2,3,5,6-Tetrafluoro-4-hydroxystyryl)-1-methylquinolinium iodide (12g). $^1$H-NMR (400 MHZ, DMSO (d6)): 9.02 (d, 5.8 Hz, 1H, Ar), 8.63 (d, 7.8 Hz, 1H, Ar), 8.41 (d, 5.4 Hz, 1H, Ar), 8.23 (dd, 7.8, 5.4 Hz, 1H, Ar), 8.11 (dd, 8.5, 7.8 Hz, 1H, Ar), 7.84 (d, 5.8 Hz, 1H, Ar), 7.22 (d, 16.1 Hz, 1H, CH=CH), 6.78 (d, 16.1 Hz, 1H, CH=CH), 4.31 (s, 3H, $^+$NCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 45.32. $^{19}$F NMR −156.27, −133.13 ppm. HRMS Calcd for $C_{18}H_{12}F_4NOI$ m/z 461.77062, Found 461.77059.

I-h (E)-2-(2,3,5,6-Tetrafluoro-4-methoxystyryl)-1-methylquinolinium iodide (12-h). The dye was not sufficiently soluble in any solvent in order to perform NMR tests. HRMS Calcd for $C_{19}H_{14}F_4NOI$ m/z 475.26041, Found 475.26039.

I-i (E)-2-(4-Dimethylaminostyryl)-1-methylquinolinium iodide (I-i). $^1$H-NMR (400 MHZ, DMSO (d6)): 9.11 (d, 5.89 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 1H, Ar), 4.42 (s, 3H, $^+$NCH$_3$), 3.01 (s, 6H, N(CH$_3$)$_2$). 157.71, 157.32, 142.85, 132.54, 130.83, 130.52, 129.98, 129.54, 128.14, 126.91, 126.71, 125.02, 123.82, 119.87, 116.16, 115.95, 46.92, 41.39. HRMS Calcd for $C_{20}H_{21}N_2I$ m/z 416.71421, Found 416.71409.

I-j (E)-2-(2,4-Dihydroxystyryl)-1-methylquinolinium iodide (I-j). $^1$H-NMR (400 MHz, DMSO (d6)): 9.02 (d, 5.89 Hz, 1H, Ar), 8.68 (d, 8.5 Hz, 1H, Ar), 7.93 (d, 16.1 Hz, 1H, CH=CH), 7.91 (d, 16.1 Hz, 1H, CH=CH), 7.8 (d, 7.8 Hz, 1H, Ar), 7.57 (d, 5.8 Hz, 1H, Ar), 7.29 (s, 1H, Ar), 7.17 (s, 1H, Ar), 7.16 (dd, 8.5, 7.8 Hz, 1H, Ar), 6.95 (d, 8.72 Hz, 2H, Ar), 6.64 (s, 1H, Ar), 4.31 (s, 3H, $^+$NCH$_3$). $^{13}$C NMR (ppm): 160.6, 157.42, 146.32, 140.05, 139.51, 136.83, 133.44, 126.08, 125.84, 125.61, 124.91, 124.03, 123.99, 123.82, 122.87, 119.35, 118.95, 111.77, 46.02. HRMS Calcd for $C_{18}H_{15}BrNOI$ m/z 405.13662, Found 405.13648.

I-k (E)-2-(2-Hydroxy-3-methoxy-5-nitrostyryl)-1-methylquinolinium iodide (I-k). The dye was not sufficiently soluble in any solvent in order to perform NMR tests. HRMS Calcd for $C_{19}H_{17}N_2O_4I$ m/z 464.26553, Found 464.25919.

(I-l)

(E)-2-(4-Hydroxy-3-nitrostyryl)-1-methylquinolinium iodide (I-l). $^1$H-NMR (400 MHz, DMSO (d6)): 9.06 (d, 5.89 Hz, 1H, Ar), 8.68 (d, 8.5 Hz, 1H, Ar), 8.43 (d, 16.1 Hz, 1H, CH=CH), 7.91 (d, 16.1 Hz, 1H, CH=CH), 7.8 (d, 7.8 Hz, 1H, Ar), 7.66 (dd, 8.5, 7.8 Hz, 1H, Ar), 7.57 (d, 5.8 Hz, 1H, Ar), 7.31 (d, 8.72 Hz, 2H, Ar), 7.16 (dd, 8.5, 7.8 Hz, 1H, Ar), 6.95 (d, 8.72 Hz, 1H, Ar), 4.31 (s, 3H, $^+$NCH$_3$). $^{13}$C NMR (ppm): 157.81, 153.33, 147.45, 146.94, 139.83, 136.62, 133.44, 129.98, 126.14, 125.14, 124.91, 123.76, 123.09, 122.12, 118.67, 117.46, 112.65, 45.32. HRMS Calcd for $C_{18}H_{15}N_2O_3I$ m/z 434.02911, Found 434.028922.

The process of preparation under microwave irradiation according to the present invention is superior to carrying the reaction of compounds (II) and (III) in the presence of a base and refluxing in a suitable alcohol (prior art) as apparent in Table 1. Yield is higher (90-98% compared to 27-85%) and reaction time shortened significantly to 5-30 minutes compared to 9-20 hours.

TABLE 1

Methos of synthesis-present invention (microwave) and conventional reflux of solvent

| | Microwave condition in EtOH | | | Normal condition in EtOH | | |
|---|---|---|---|---|---|---|
| Product | Yield (%) | Reaction time (min) | Temperature (° C.) | Yield (%) | Reaction time (h) | Temperature (° C.) |
| I-a | 94 | 15 | 70 | 65 | 9 | Reflux |
| I-b | 96 | 25 | 80 | 53 | 6 | Reflux |
| I-c | 91 | 10 | 75 | 27 | 12 | Reflux |
| I-d | 95 | 15 | 75 | 55 | 12 | Reflux |
| I-e | 99 | 5 | 75 | 85 | 9 | Reflux |
| I-f | 90 | 10 | 75 | 73 | 14 | Reflux |
| I-g | 99 | 5 | 75 | 45 | 10 | Reflux |
| I-h | 95 | 15 | 80 | 37 | 16 | Reflux |
| I-i | 98 | 5 | 80 | 81 | 8 | Reflux |
| I-j | 94 | 20 | 80 | 64 | 12 | Reflux |
| I-k | 91 | 30 | 80 | 60 | 18 | Reflux |
| I-l | 90 | 30 | 80 | 59 | 20 | Reflux |

Physical Properties

Example 2: Solubility in Various Polar Solvents

Figure 1:
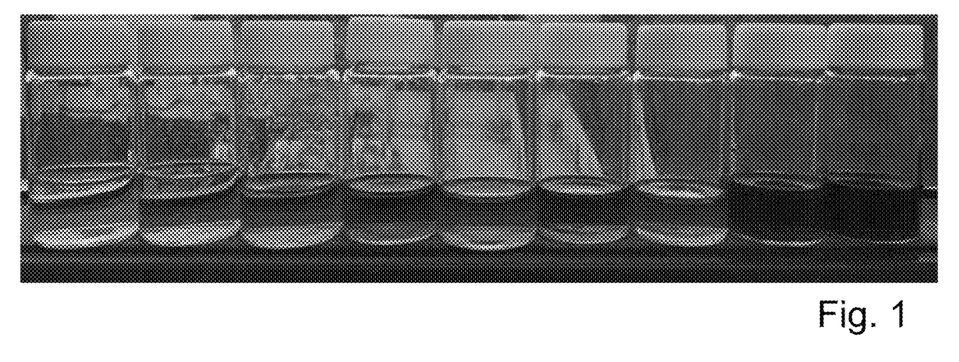
FIG. 1 provides evidence for variance of color of the solution solubilizing a compound of the present invention (I-e) depending on the solvent and its polarity. The solvents are (left to right): acetic acid, water, methanol, ethanol, isopropanol, DMSO, DMF, acetone and dichloromethane.

The compounds (I-a-I-l) are soluble in nonpolar organic solvents only to a rather limited extent, while they are readily soluble in polar organic solvents. Some are readily soluble in water. In polar solvent such as water, the zwitterion form of the compounds dominates, while in nonpolar solvents such as chloroform, the neutral form prevails. More particularly, styryl quinolinium compounds having a hydroxyl group at the para position of the styryl moiety, are soluble in a wide range of solvents giving colored solutions, the color of which is solvent-dependent. Turning to FIG. 1, color change of the solution depending on the polarity of the solvent dissolving compound I-e is presented where compound I-e is dissolved in (from left to right): acetic acid, water, methanol, ethanol, isopropanol, DMSO, DMF, acetone and dichloromethane.

Example 3: Absorption Wavelength

The styryl quinolinium compounds of formula (I) are characterized by $\Delta_{abs}$ of 440-658 nm; $\lambda_{em}$ of 485-715 nm; and $\Sigma-$ of 12,200-49,000 $M^{-1}$ $cm^{-1}$ at polar solvents having polarity values between 1 to 0.355. The more polar the solvent is, the shorter is the absorption wavelength of the dye. Table 2 provides photophysical properties of the compounds (I-a-I-l) in various solvents at a range of relative polarity values; between 1 (water) to 0.355 (acetone).

TABLE 2

Photophysical properties of derivatives I-a-I-l.

| Dye | $\lambda_{Abs}$ (nm) | $\epsilon$ ($M^{-1}cm^{-1}$) | $\epsilon_{em}$ (nm) | Dye | $\lambda_{Abs}$ (nm) | $\epsilon$ ($M^{-1}cm^{-1}$) | $\lambda_{em}$ (nm) |
|---|---|---|---|---|---|---|---|
| Water | | | | MeOH | | | |
| I-a | 460 | 21200 | 515 | 12a | 475 | 22100 | 525 |
| I-b | 438 | 20700 | 501 | 12b | 440 | 19900 | 490 |
| I-c | 508 | 26300 | 560 | 12c | 560 | 27200 | 610 |
| I-d | 502 | 24900 | 555 | 12d | 508 | 24900 | 600 |
| I-e | 520 | 45800 | 605 | 12e | 535 | 46100 | 670 |
| I-f | 515 | 41200 | 580 | 12f | 520 | 40900 | 648 |
| I-g | 503 | 23300 | 518 | 12g | 505 | 23800 | 591 |
| I-h | 478 | 22900 | 508 | 12h | 490 | 22900 | 580 |
| I-i | 510 | 29800 | 575 | 12i | 530 | 30300 | 665 |
| I-j | 470 | 19200 | 503 | 12j | 478 | 18600 | 500 |
| I-k | 440 | 16400 | 495 | 12k | 445 | 17400 | 495 |
| I-l | 475 | 13300 | 499 | 12l | 480 | 12200 | 500 |
| EtOH | | | | DMSO | | | |
| I-a | 480 | 21900 | 525 | I-a | 490 | 23500 | 528 |
| I-b | 450 | 21300 | 495 | I-b | 465 | 20600 | 501 |
| I-c | 565 | 27100 | 640 | I-c | 566 | 25700 | 660 |
| I-d | 510 | 28200 | 605 | I-d | 520 | 23600 | 610 |
| I-e | 556 | 49000 | 685 | I-e | 600 | 44700 | 715 |
| I-f | 548 | 41200 | 665 | I-f | 591 | 42100 | 675 |
| I-g | 509 | 23900 | 625 | I-g | 499 | 22950 | 603 |
| I-h | 506 | 22700 | 608 | I-h | 500 | 20900 | 595 |
| I-i | 544 | 31000 | 675 | I-i | 590 | 30100 | 703 |
| I-j | 480 | 17900 | 495 | I-j | 480 | 18400 | 500 |
| I-k | 460 | 16900 | 495 | I-k | 450 | 17900 | 501 |
| I-l | 485 | 13900 | 506 | I-l | 485 | 12200 | 509 |
| DMF | | | | Aceton | | | |
| I-a | 490 | 21500 | 520 | I-a | 90 | 19900 | 520 |
| I-b | 460 | 21100 | 500 | I-b | 55 | 18100 | 505 |
| I-c | 555 | 28100 | 660 | I-c | 10 | 27600 | 628 |
| I-d | 519 | 25000 | 610 | I-d | 90 | 26300 | 605 |
| I-e | 599 | 44900 | 715 | I-e | 50 | 47100 | 702 |
| I-f | 590 | 41100 | 675 | I-f | 90 | 44500 | 685 |
| I-g | 495 | 22100 | 603 | I-g | 00 | 23200 | 590 |
| I-h | 500 | 23400 | 595 | I-h | 05 | 22900 | 590 |
| I-i | 588 | 29800 | 705 | I-i | 80 | 28300 | 695 |
| I-j | 482 | 19200 | 503 | I-j | 60 | 18700 | 495 |
| I-k | 450 | 16400 | 500 | I-k | 90 | 15800 | 515 |
| I-l | 485 | 11100 | 505 | I-l | 80 | 12200 | 508 |

Example 4: pH Dependence of Absorption and Emission

The absorption and emission wavelengths of the styryl quinolinium compounds of formula (I) containing OH/NMe$_2$ groups in the para position of the styryl moiety is pH dependent. A red-shift of the wavelengths of absorption and emission is obtained in basic vs. acidic medium. The styryl quinolinium compounds of formula (I) are further characterized by quantum yield that is dependent on the viscosity of the solvent. The more polar the solvent is, the shorter is the absorption wavelength of the dye. Table 3 provides values of absorption and emission wavelengths of compounds I-a-I-l that as evident depend on the pH. A red-shift of the wavelengths of absorption and emission was obtained in basic vs. acidic medium

TABLE 3

The absorption and emission wavelengths of compounds I-a-I-l depending on the pH.

| Dye | $\lambda_{abs}$ (nm) pH 2 | $\lambda_{abs}$ (nm) pH 10 | $\lambda_{em}$ (nm) pH 2 | $\lambda_{em}$ (nm) pH 10 |
|---|---|---|---|---|
| I-a | 460 | 467 | 515 | 522 |
| I-b | 438 | 438 | 501 | 500 |
| I-c | 508 | 512 | 560 | 564 |
| I-d | 502 | 502 | 555 | 556 |
| I-e | 520 | 531 | 605 | 608 |
| I-f | 515 | 515 | 580 | 580 |
| I-g | 503 | 501 | 518 | 520 |
| I-h | 478 | 478 | 508 | 508 |
| I-i | 510 | 508 | 575 | 578 |
| I-j | 470 | 475 | 503 | 500 |
| I-k | 440 | 447 | 495 | 499 |
| I-l | 475 | 477 | 499 | 502 |

Example 5: Photostability of Compounds

Figure 2:
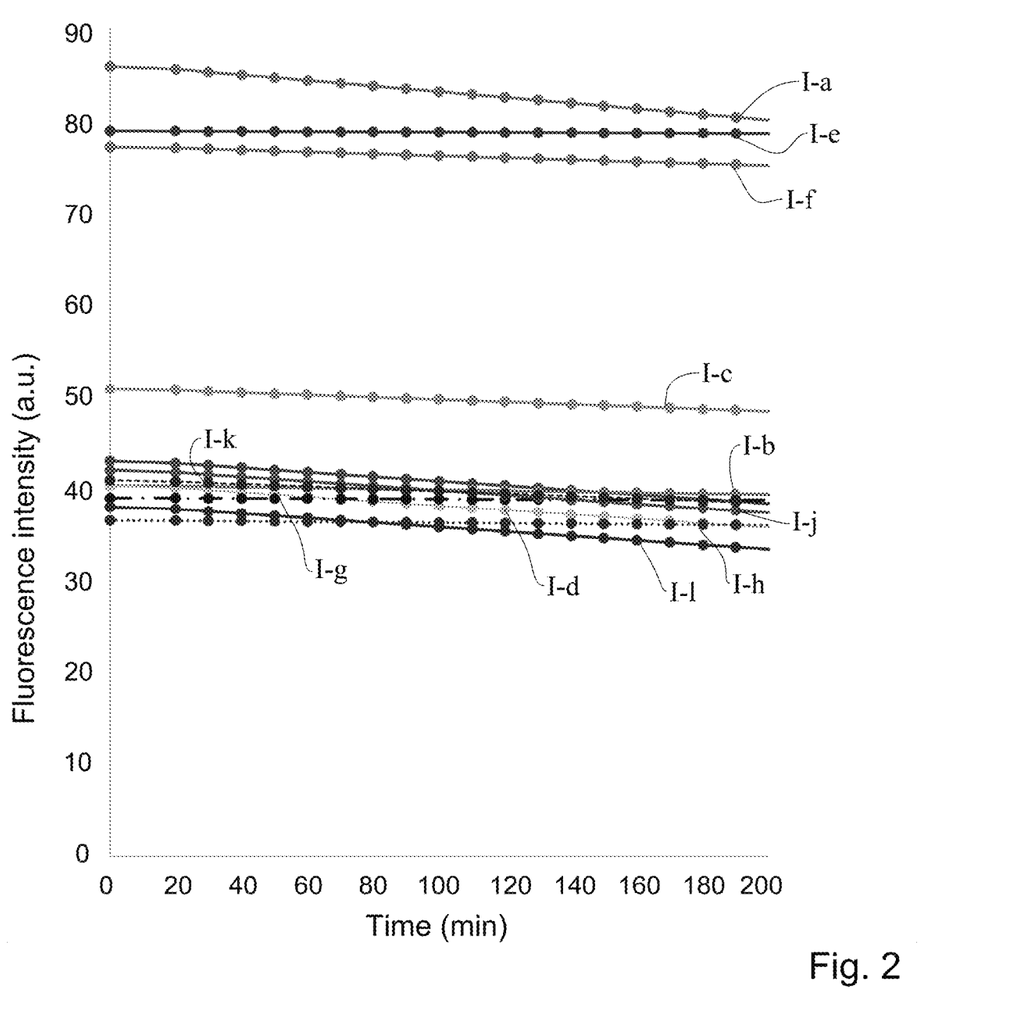
FIG. 2 demonstrates the photostability of dyes I-a-I-l measured by the loss of fluorescence intensity (2 μM dye, in PBS buffer).

Turning to FIG. 2, the photostability of compounds of the present invention is provided by demonstrating the measured loss of fluorescence intensity of dyes I-a-I-l. FIG. 2 clearly demonstrates that the styryl quinolinium compounds of formula (I) are photostable, for up to 200 minutes of irradiation (96% remaining). The photostability of dyes I-a-I-l was tested by exposure to a light source of a Cary Eclipse Fluorescence Spectrophotometer (ex 500-650 nm), with the exclusion of ambient light. 2 μM of the Compound in phosphate buffer solution were irradiated for 200 min, with an assessment of their fluorescence intensity at five-minute intervals.

Results after a 200-minute irradiation in PBS buffer as provided in FIG. 2 demonstrate in a clear manner that the fluorescence intensity of dyes I-a-I-l was not affected by the irradiation. The remaining emission percentages of the dyes after 200 min were: I-a (89%), I-b (93%), I-c (91%), I-d (88%), I-e (96%), I-f (92%), I-g (95%), I-h (93%), I-i (95%), I-j (88%), I-k (94%) and I-l (87%).

Example 6: Quantum Yield

The quantum yields of compounds of formula (I) of the present invention were found to vary. The fluorescence quantum yields of the compounds (I) were determined relative to rhodamine B in ethanol at 25° C. The quantum yield was calculated according to the following equation:

$$\Phi_F = \Phi_R I / I_R * OD_R / OD * \eta^2 / \eta_R$$

Here, $\Phi$ and $\Phi_R$ are the fluorescence quantum yield of the sample and the reference, respectively, $I$ and $I_R$ are areas under the fluorescence spectra of the sample and of the reference, respectively, $OD$ and $OD_R$ are the absorption values of the sample and the reference at the excitation wavelength, and $\eta$ and $\eta_R$ are the refractive index for the respective solvents used for the sample and the reference. The photostability of all the dyes was tested by exposure to a light source of a Cary Eclipse Fluorescence Spectrophotometer, with the exclusion of ambient light. 2 μM Dye solutions in PBS were irradiated for 200 min, with an assessment of their fluorescence intensity at five-minute intervals.

In particular, the quantum yield of compounds I-a-I-l was found to depend on the viscosity of the solvent. The more polar the solvent is, the shorter is the absorption wavelength of the compound. An example of the quantum yields of the compounds I-a-I-l that were measured in water and glycerol is shown in the Table 4 below:

TABLE 4

| Quantum yield in water and glycerol | | |
|---|---|---|
| Compound | $\Phi^a$ (water) % | $\Phi^a$ (glycerol) (%) |
| I-a | 0.69 | 2.13 |
| I-b | 0.61 | 1.74 |
| I-c | 0.94 | 2.84 |
| I-d | 0.87 | 3.47 |
| I-e | 1.77 | 5.55 |
| I-f | 1.61 | 4.89 |
| I-g | 0.62 | 1.68 |
| I-h | 0.48 | 1.09 |
| I-i | 1.07 | 3.74 |
| I-j | 0.79 | 2.91 |
| I-k | 0.11 | 0.31 |
| I-l | 0.28 | 0.92 |

The toxicity of the compounds on T lymphocytes was evaluated by flow cytometry. Cell death was measured by fluorescence-activated cell sorting (FACS), which is a powerful and precise tool for measurement of a single cell within a population. The cell death was checked before adding the compounds and 3 hours after the addition of the dyes. Compounds I-c, I-i and I-e were not toxic for a period of 3 hours.

The styryl quinolinium compounds of formula (I) stain the nucleoli and the cytoplasm of fixed and living cells. Preferably, the compounds bind to rRNA in the nucleolus and the cytoplasm. In some embodiments, does not stain nuclear dsDNA and binds histones-free DNA extract. The styryl quinolinium compounds of formula (I) may stain the nucleoli rapidly, in about 150 seconds.

Staining and Probing of Cells.

General

Cell Culture

Human U2OS cells were cultured under standard conditions at 37° C., 5% $CO_2$, in low glucose Dulbecco's modified Eagle's medium (DMEM, Biological Industries, Israel) containing 10% fetal bovine serum (FBS, HyClone), and 4 mM Glutamine, 100 IU/mL Penicillin, and 100 μg/mL Streptomycin (Biological Industries). HeLa, HEK293, and mouse embryonic fibroblasts (MEF) were maintained in high glucose DMEM containing 10% FBS, and 100 IU/mL Penicillin, and 100 μg/mL Streptomycin. For RNase digestion, cells were treated with 5 μg/ml actinomycin D (Sigma) for 3 hrs, then fixed in ice cold methanol for 2 min, and digested with RNase (100 mg/ml in PBS with 3 mM $MgCl_2$, Sigma) for 45 min at room temperature. For DNase treatment, cells were first fixed in ice cold methanol for 2 min, and then incubated (100 mg/ml, 5 mM $MgCl_2$) for 2 hrs at room temperature. Nuclei were counterstained with 1 μM Hoechst 33342 (Sigma) and coverslips were mounted in mounting medium.

Immunofluorescence

Cells were grown on coverslips, washed with PBS and fixed for 20 min in 4% PFA. Cells were then permeabilized in 0.5% Triton X-100 for 2.5 min. Cells were washed twice with PBS and blocked with 5% BSA for 20 min, and immunostained for 1 hr with a primary antibody. After three washes with PBS, the cells were incubated for 1 hr with secondary fluorescent antibodies. Primary antibodies: mouse anti-G3BP1 (Abcam) and rabbit anti-fibrillarin (Abcam). Secondary antibodies: Alexa Fluor 488 goat anti-mouse (Abcam) Alexa Flour 488 goat anti-rabbit (Abcam). Cells were then stained with compound I-e (10 μg/mL). Nuclei were counterstained with 1 μM Hoechst 33342 (Sigma) and coverslips were mounted in mounting medium.

Fluorescence Microscopy

For spectral scanning, an inverted Leica SP8 scanning confocal microscope, driven by the LASX software (Leica Microsystems, Mannheim, Germany) and equipped with a super-continuum white light laser, was used. A lambda-lambda scan was performed with the software, with a PL APO 63x/1.40 OIL objective. After export, images were analysed with Cell Profiler to measure the intensity of the images, and data was exported to Excel and plotted. For live cell imaging, a Leica DMI8 wide-field inverted microscope was used, equipped with a Leica sCMOS camera and $CO_2$/incubation system. Cells were imaged every 5 seconds for the short time course, and every 15 min for the longer time course. Wide-field fluorescence images of fixed cells were obtained using the Cell^R system based on an Olympus IX81 fully motorized inverted microscope (60X PlanApo objective, 1.42 NA) fitted with an Orca-AG CCD camera (Hamamatsu) driven by the Cell® software. ImageJ software was used when measuring the signal-to-noise ratio graph by acquiring the intensity of several pixels from each time point.

RNA Extraction

Total RNA was produced by using Tri-Reagent (Sigma), and DNA was removed using Turbo-DNase free kit (Invitrogen). 2 µg of total RNA extracts from HeLa cells were separated by electrophoresis in a 1% agarose gel. The rRNA 28S and 18S bands were extracted separately from the smeared mRNA in the gel. RNAs were cleaned with a Nucleospin gel and PCR clean up kit (Macherey-Nagel).

DNA and Chromatin Protein Extraction

Genomic DNA lacking nucleosomes was purified from HEK293 cells using the TIANamp Genomic kit (TIANGEN, China). Genomic DNA including nucleosomes was purified from HEK293T cells as follows. Cells were washed with PBS and collected at 500× g for 5 min and then lysed in Nonidet P-40 lysis buffer (25 mM Tris-HCl, pH 7.4, 150 mM NaCl, 10% glycerol and 1% Nonidet P-40) with a protease inhibitor cocktail (1:100 dilution) at 4° C. for 5 min. After centrifugation at 15,000×g for 5 min, the pellets were collected and washed with Nonidet P-40 lysis buffer. Then Nonidet P-40 lysis buffer with micrococal nuclease (1:100 BioLabs), 5 mM $CaCl_2$) and a protease inhibitor cocktail (1:100 dilution) were added to the pellets and incubated at 25° C. for 10 min. 10 mM EGTA was added to stop the reaction. After centrifugation at 15,000×g for 15 min, the supernatant containing the chromatin were collected.

Example 7: Compound I-e Binds RNA in Solution

Figure 3:
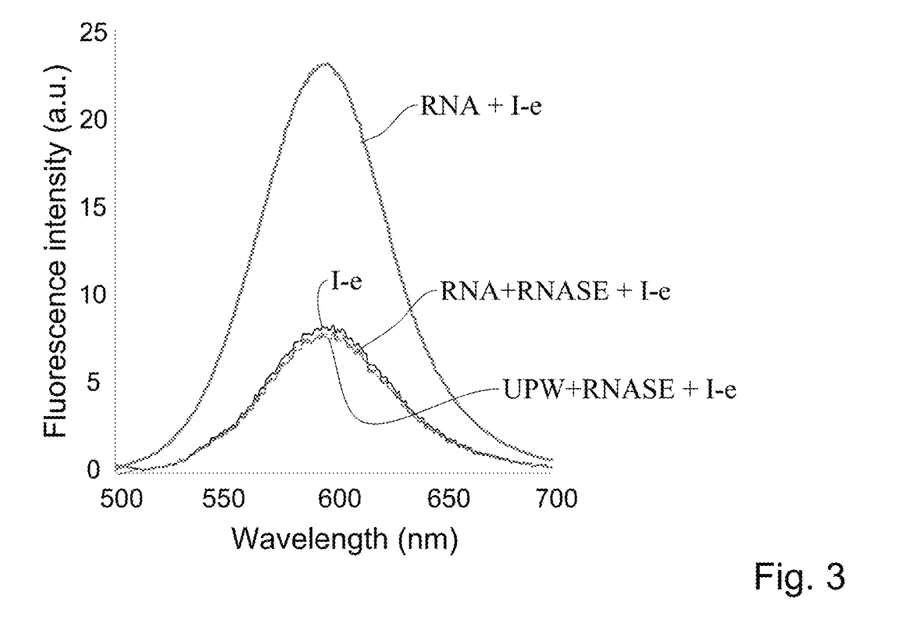
FIG. 3 provides emission spectra of compound I-e with RNA in water. Compound I-e alone (black), RNA solution+compound I-e (blue), compound I-e+ RNA solution+RNASE, control, (green), water+RNASE, control, (red).

Binding of dye I-e to RNA was tested by adding this dye to an RNA solution extracted from human cells (as described above) and evaluating the increase in fluorescence intensity. Notably, a significant, 3.1-fold increase in fluorescence intensity was observed once compound I-e interacted with total RNA extract. FIG. 3 shows the Emission spectra of probe I-e with RNA in water. Compound I-e alone, RNA solution+ Compound I-e, Compound I-e+ RNA solution+ RNASE, control, water+RNASE, control.

Compound I-e Stains Fixed Cells

Figure 4A:
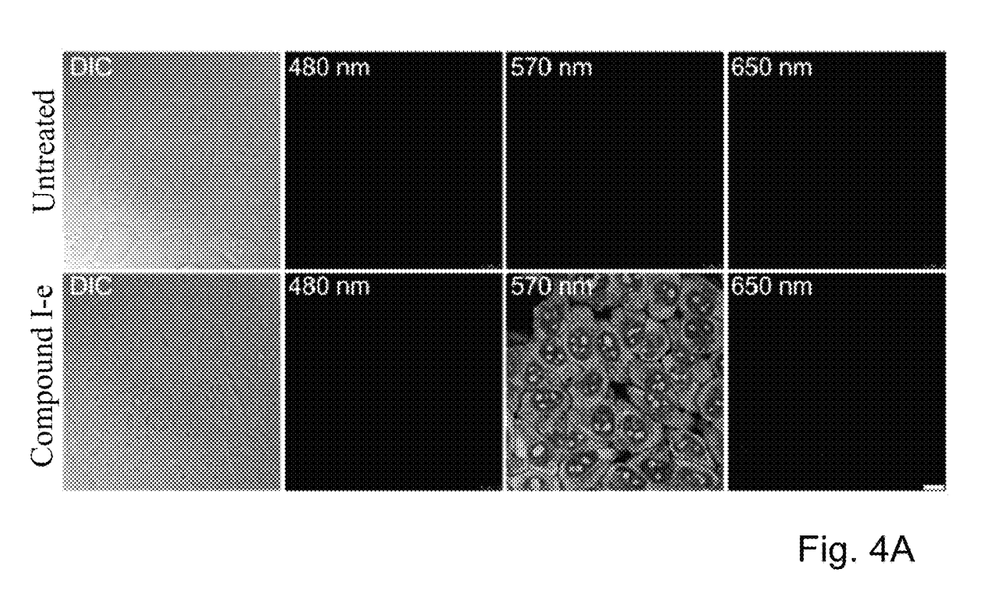
FIG. 4A; compound I-e was added to HeLa cells and these were scanned as described in the Methods section. The strongest excitation, at the emission range of 647-667 nm was found to be 570 nm. Bar=10 μm.
Figure 4B:
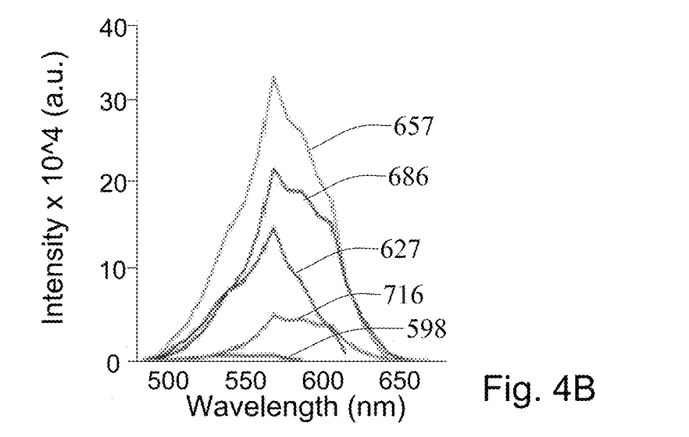
FIG. 4B; images were analyzed as described in the Methods and the image emission intensities were plotted. The excitation that resulted in the strongest emission was found to be at 570 nm.
Figure 4C:
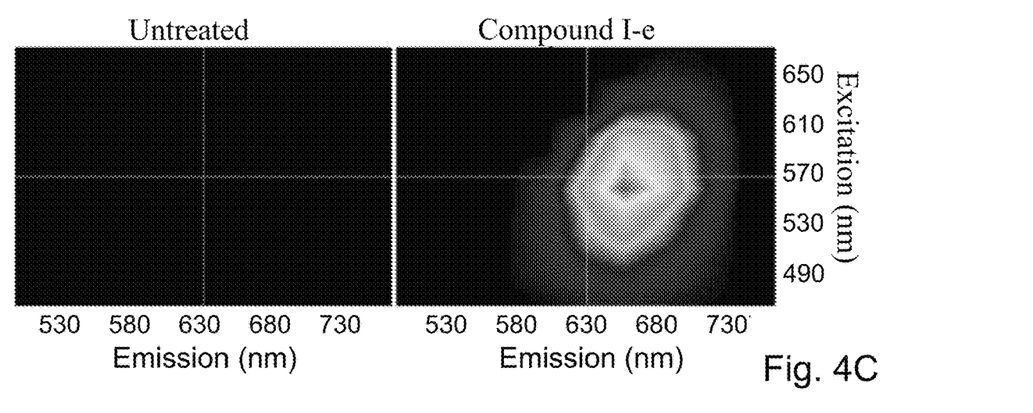
FIG. 4C; 2D heat map exported from acquisition software showing the excitation vs. the emission profiles.
Figure 4D:
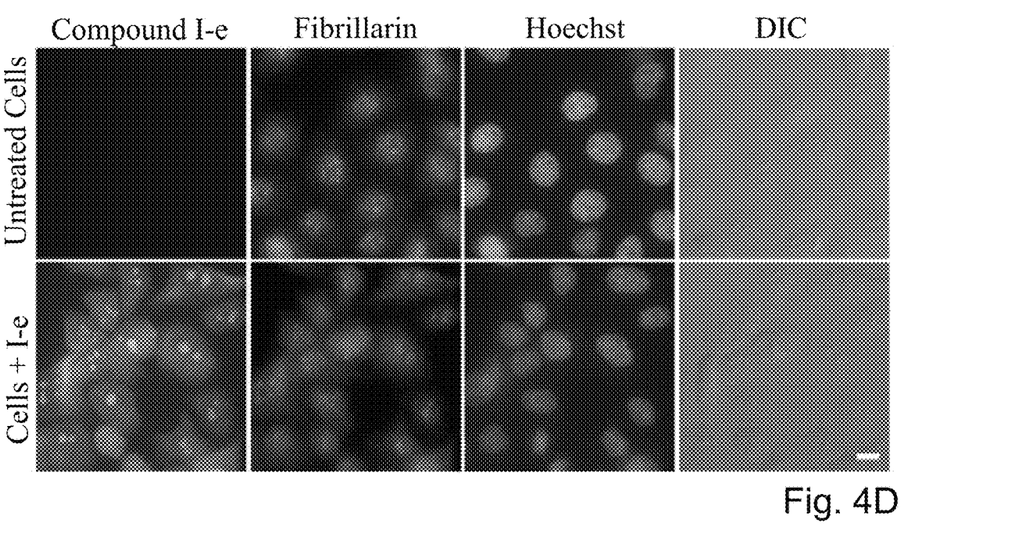
FIG. 4D; compound I-e localizes to nucleoli in treated cells. Nucleoli are identified by staining with an antibody to the nucleolar marker fibrillarin (green). Hoechst DNA stain is in cyan. No 12e signal is detected in untreated cells. Bar=10 μm.

The fluorescent properties of the compound I-e in cells were analyzed. Compound I-e was applied to fixed HeLa cells. A lambda-lambda scan, using a scanning confocal microscope equipped with a supercontinuum laser and tunable detection, was done to determine the excitation-emission spectrum of the compound. The peak fluorescent intensity was at the emission range of 647-667 nm and optimal excitation at 570 nm. This clearly showed the detection of the cells as shown in FIGS. 4A-4B. Spectrum scan shows peak of excitation/emission. FIG. 4A shows that following the addition of Compound I-e to HeLa cells these were scanned as described in the Methods section (above). The strongest excitation, at the emission range of 647-667 nm was found to be 570 nm. Bar=10 µm. FIG. 4B demonstrates the analysis of images as described in the Methods (above) and the image emission intensities were plotted. The excitation that resulted in the strongest emission was found to be at 570 nm. FIG. 4C provides a 2D heat map exported from acquisition software showing the excitation vs. the emission profiles. FIG. 4D demonstrates that Compound I-e localizes to nucleoli in treated cells. Nucleoli are identified by staining with an antibody to the nucleolar marker fibrillarin (green). Hoechst DNA stain is in cyan. No I-e signal is detected in untreated cells. Bar=10 µm.

Example 8: Staining of Cells

Staining Living Cells with Compound I-e

Figure 5A:
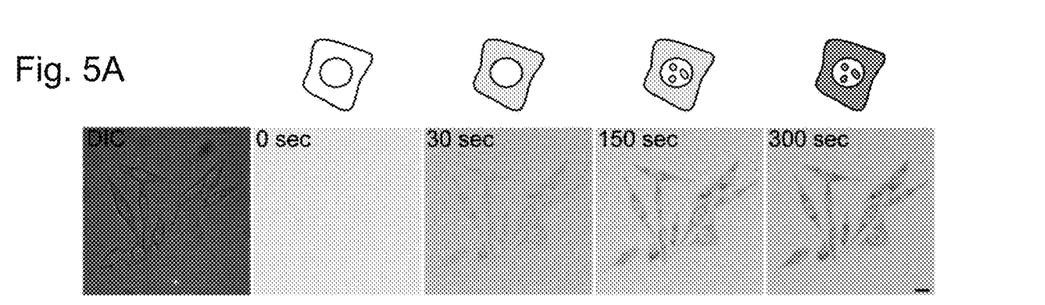
FIG. 5A; Cells were imaged every 5 sec for 5 min. The compound entered the cells within 30 sec and stained nucleoli within 150 sec.
Figure 5B:
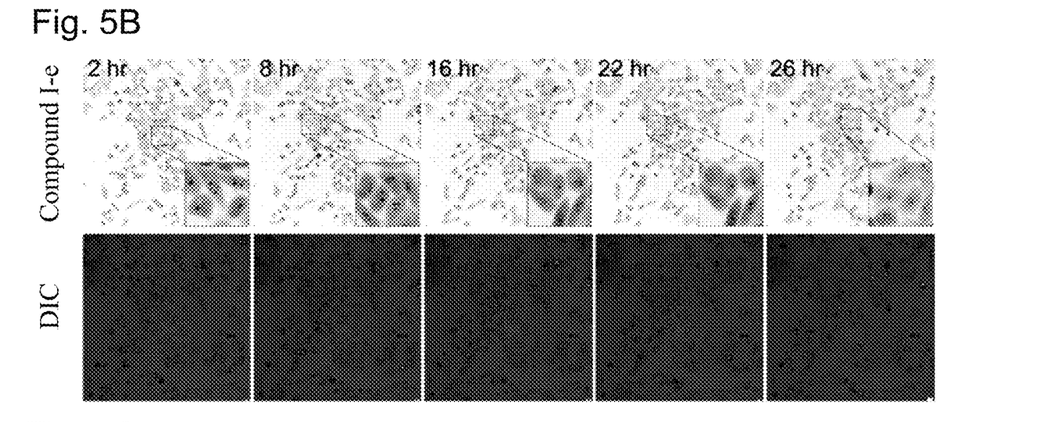
FIG. 5B; Cells were then imaged every 15 min for 26 hours and the compound intensity remained strong and specific to the nucleoli. The cells remained viable. Bar=20 μm.
Figure 5C:
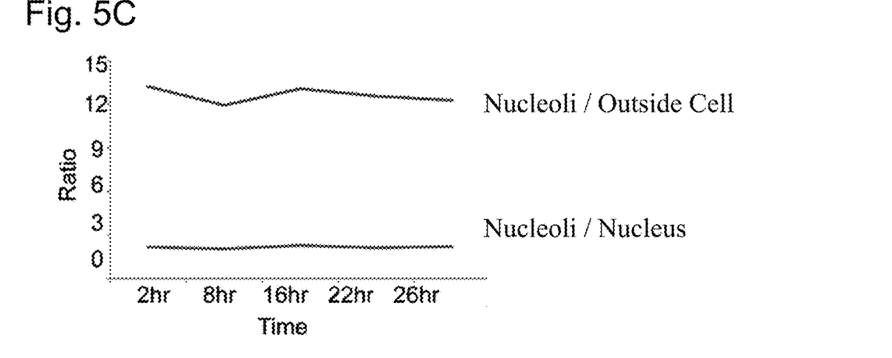
FIG. 5C; Signal-to-noise ratio pixel intensity graph of nucleoli/nucleus and nucleoli/outside of the cell derived from ImageJ software.

Compound I-e is highly cell permeable. Within 30 seconds the compound was detected in the cytoplasm, and within 150 seconds the compound stained nucleoli (FIG. 5A). Additionally, compound I-e could be applied to living cells for over 24 hours without affecting viability, cell morphology, or proliferation as cell divisions continuously occurred indicating that compound I-e is not toxic to cells (FIG. 5B). Notably, compound I-e remained fluorescently stable, bright and specifically bound to nucleoli (FIG. 5B), with a high signal-to-noise ratio (FIG. 5C).

Example 9: Staining Fixed Living Cells

Staining Fixed and Living Cells with Compound I-e

Figure 6A:
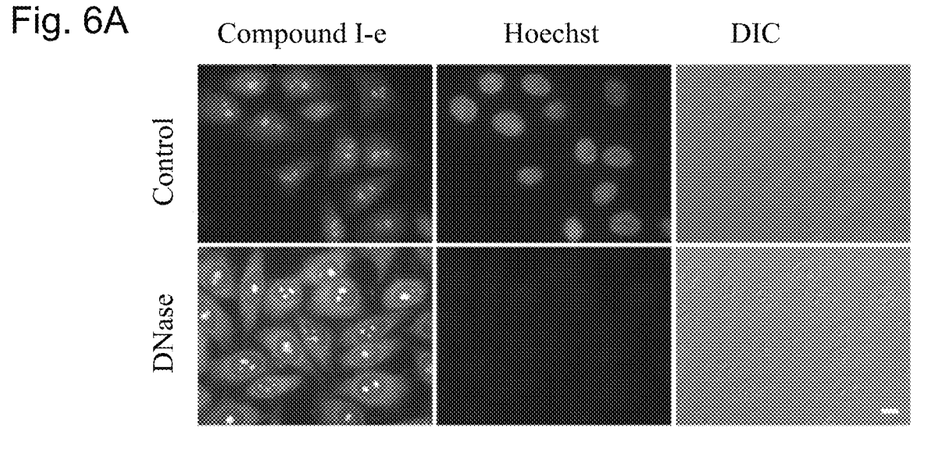
FIG. 6A; Wide-field fluorescence images of untreated or DNase treated cells stained with the compound I-e. Hoechst DNA stain is in cyan.
Figure 6B:
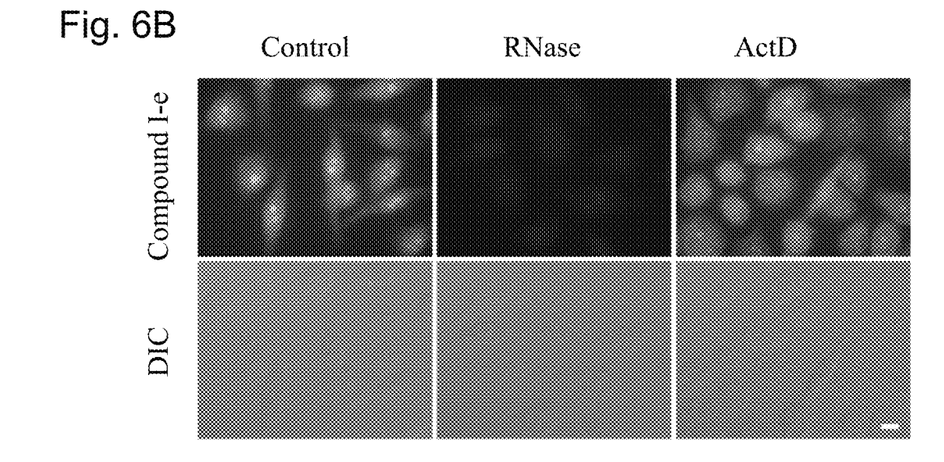
FIG. 6B; Untreated cells or cells treated with RNase or with the actinomycin D transcriptional inhibitor. DIC images are in grey. Bar=10 μm.

The binding of compound I-e to nucleic acids within cells was investigated. To this end, fixed and stained cells were treated with either deoxyribonuclease (DNase) or ribonuclease (RNase) to remove DNA or RNA from cells, respectively (FIG. 6). While with the treatment with DNase no considerable loss of fluorescence signal was observed (FIG. 6A), after RNase treatment, cytoplasmic and nucleolar fluorescence signal disappeared in comparison to untreated cells (FIG. 6B). These digestion experiments validated the preference of compound I-e to attach to RNA since cells in which the RNA was removed by RNase, did not stain anymore. When the cells were treated with actinomycin D, an inhibitor of RNA polymerase II that transcribes mRNA (and not rRNA), there was not much change in the intensity of the dye in the cells, suggesting that the dye preferably binds to rRNA in the nucleolus and the cytoplasm.

Figure 7A:
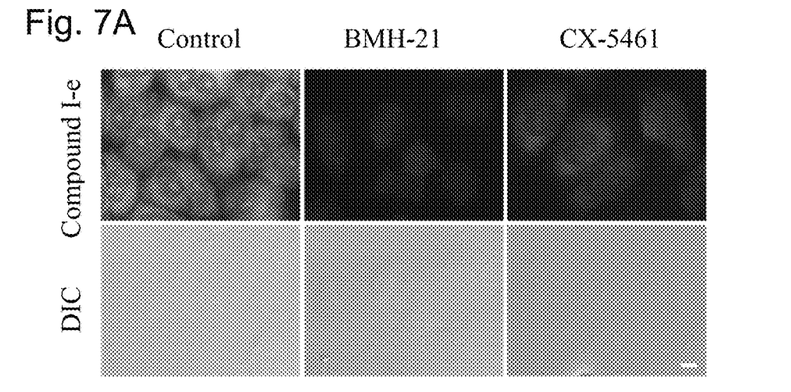
FIG. 7A; transcriptional inhibition of RNA polymerase I by CX-5461 and BMH-21 diminishes the fluorescence signal of compound I-e in cells.
Figure 7B:
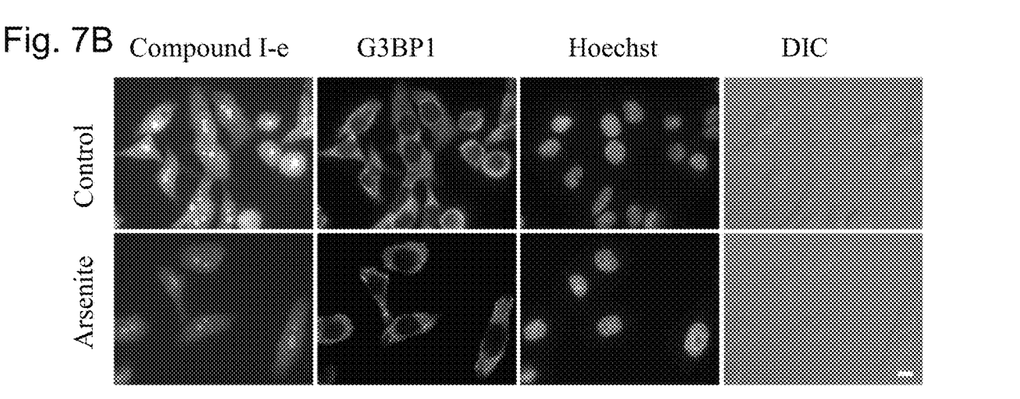
FIG. 7B; stress granules formed by arsenite treatment and labeled with anti-G3BP1 (green) do not contain compound I-e (white). Hoechst DNA stain is in cyan. DIC is in grey. Bar=10 μm.

The interaction of compound I-e with rRNA was tested, nucleolar rRNA transcription was inhibited by inhibiting RNA polymerase I activity with two specific inhibitors (FIG. 7A). Following these treatments, the fluorescent signal throughout the nucleoli and the cytoplasm was significantly reduced. Further the assembly of cytoplasmic stress granules that contain mRNAs but not rRNAs was induced. This way foci containing mRNAs were formed in the cytoplasm, which might be detectable by the compound if it binds mRNA. Stress granules were formed by the addition of arsenite to the cells. However, the compound did not localize with stress granules, implying that compound I-e is not binding to cytoplasmic mRNA (FIG. 7B).

Example 10: Preference to Secondary Structures in the rRNA

Figure 8:
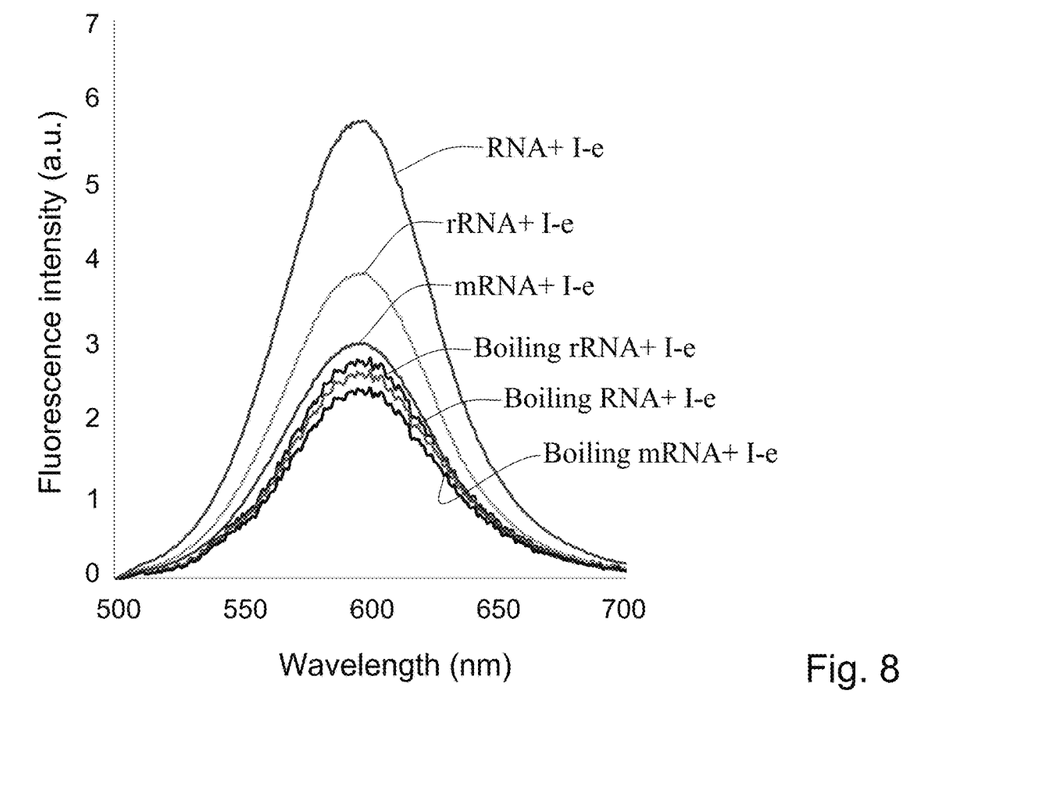
FIG. 8. Provides evidence that compound I-e binds to secondary structures in rRNA. The binding of compound I-e to rRNA and mRNA in solution at room temperature and at 90° C. In the presence of structured rRNA there is an increase in the fluorescent signal; however, when the samples were heated and the secondary structures of the rRNA are dismantled, then no increase in fluorescence was observed.

Compound I-e was found to have preference to secondary structures in the rRNA:

rRNA and mRNA were purified from total cell RNA extracts. The binding of the compound to these RNAs under two conditions was examined. At room temperature the secondary structures are preserved, and strong binding to rRNA was observed (FIG. 8) as measured by fluoresce (increase of fluorescence). Once the secondary structures of the RNA were destroyed by heating the RNAs to 90° C., the binding to the rRNA was lost (no increase in fluorescence was observed), indicating that indeed compound I-e binds the complex secondary structures of rRNA.

Example 11: Binding of Compound I-e to Histones-Free DNA Extract

Figure 9:
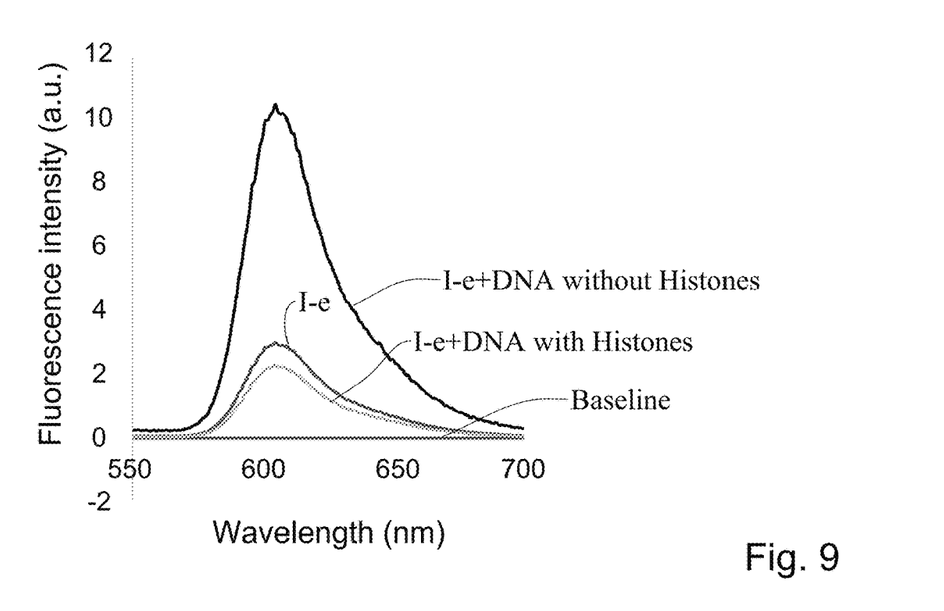
FIG. 9. Provides fluorescence spectra evidencing the binding of compound I-e to DNA without histones

Compound I-e binds secondary structures in the rRNA that are probably double stranded (ds) however nuclear dsDNA was not stained as well since histones forming the nucleosomes on the DNA in cells might mask the binding of the dye. DNA from cells, with or without histones, was extracted. Compound I-e did not bind to DNA with histones and could bind only to DNA extract in which the histones were removed (FIG. 9).

The invention claimed is:

1. The compound (E)-2-(3, 5-Difluoro-4-hydroxystyryl)-1-methylquinolinium iodide (I-e).

2. A method for imaging rRNA, comprising adding the compound of claim 1 to a sample containing rRNA, and imaging the fluorescence.

* * * * *